US008647698B2

(12) United States Patent
Kusano et al.

(10) Patent No.: US 8,647,698 B2
(45) Date of Patent: Feb. 11, 2014

(54) IMMUNOPOTENTIATING FERMENTED FOOD OBTAINED FROM FRUCTAN-CONTAINING FOOD

(75) Inventors: Shuichi Kusano, Sakaide (JP); Hiroshi Tamura, Marugame (JP); Takaaki Yamashita, Oshima-gun (JP)

(73) Assignee: Fuji Sangyo Co., Ltd., Marugame-shi, Kagawa (JP)

( * ) Notice: Subject to any disclaimer, the term of this patent is extended or adjusted under 35 U.S.C. 154(b) by 62 days.

(21) Appl. No.: 13/201,906

(22) PCT Filed: Feb. 15, 2010

(86) PCT No.: PCT/JP2010/052139
§ 371 (c)(1),
(2), (4) Date: Aug. 17, 2011

(87) PCT Pub. No.: WO2010/098217
PCT Pub. Date: Sep. 2, 2010

(65) Prior Publication Data
US 2012/0027914 A1 Feb. 2, 2012

(30) Foreign Application Priority Data

Feb. 27, 2009 (JP) .................................. 2009-044982

(51) Int. Cl.
*A23L 1/212* (2006.01)

(52) U.S. Cl.
USPC ............ 426/637; 426/638; 426/615; 426/531

(58) Field of Classification Search
USPC .................................. 426/637, 638, 615, 531
See application file for complete search history.

(56) References Cited

FOREIGN PATENT DOCUMENTS

| EP | 1084624 A2 | 3/2001 |
|---|---|---|
| JP | 53-26361 A | 3/1973 |
| JP | 48-52995 A | 7/1973 |
| JP | 08-294379 A | 11/1996 |
| JP | 2002-154981 A | 5/2002 |
| JP | 2006-094853 A | 4/2006 |
| JP | 2007-185105 A | 7/2007 |
| JP | 2007-244211 A | 9/2007 |
| JP | 2008-231002 A | 10/2008 |
| WO | WO 2004/103083 A1 | 12/2004 |

OTHER PUBLICATIONS

JP-2006-094-853-Machine Translation.*
Niness, K. R. 1999. Nutritional and health benefints of inulin and oligofructose. J. Nutrition. 129: 1402S-1406S.*
Paludan-Müller et al., "Genotypic and phenotypic characterization of garlic-fermenting lactic acid bacteria isolated from som-fak, a Thai low-salt fermented fish product," *Journal of Appl. Microbiol.*, (2002), vol. 92, No. 2, pp. 307-314.
Eizo Kitamura et al., "Tsukemono Kojo ni Okeru Datsuen Gijutsu no Kaizen ni Kansuru Kenkyu (Dai 4 Ho) Denki Toseki ni yoru Enzo Rakkyo Sekieki kara no Yuyo Seibun no Kaishu to Riyo," "Improvement of Desalting System of Salted Water (Part IV). Utlization of Desalted Scallion Brine by Electrodialysis," *Reports of Saitama Prefectural Industrial Technology Center.* (1999), vol. 1, pp. 203-207.
Kyoichi Kobayashi, "Rakkyo Shitazuke Hakko no Anteika Gijutsu 1 Rakkyo Shitazuke Hakkoyo Nyusankin no Senbatsu to Tenka Koka," *Shokuhin Kako ni Kansuru Shiken Seiseki,* (1999), vol. 1998, pp. 21-24.
Eizo Kitamura et al., "Nyusankin no Seisei suru Fructan Bunkai Koso no Seisei to Seishitsu," "Purification and Properties of Extracellular Fructan Degarding Enzymes From Lactic Acid Bacteria," *Saitama-Ken Shokuhin Kogyo Shikenjo Gyomu Hokoku,* (1998), vol. 1997, pp. 28-38.
Kyoichi Kobayashi et al., "Nyusankin Starter o Shiyo shita Rakkyo Shitazuke Hakko no Anteika Gijutu," edited by Fukui-Ken Norin Suisanbu, Fukyu ni Utsushita Gijutsu Heisei 11-15 Nendo, (2003) pp. 61-62.
Semjonovs, P. et al., "An Influence of Fructan Containing Concentrate from Jerusalem Artichoke Tubers on the Development of Probiotic Dairy Starters on Milk and Oat-based Substrates," *Food Biotechnol.*, (2007), vol. 21, No. 3/4, pp. 349-363.
Supplementary European Search Report mailed on Oct. 15, 2012 for EP 10746098.
Paludan-Muller C. et al., "Purification and 1-5 Characterisation of an Extracellular Fructan beta-fructosidase from a *Lactobacillus pentosus* Strain Isolated from Fermented Fish", *Systematic and Applied Microbiology,* Jan. 1, 2002, pp. 13-20, vol. 25, No. 1, Urban & Fischer.

* cited by examiner

*Primary Examiner* — D. Lawrence Tarazano
*Assistant Examiner* — Hamid R Badr
(74) *Attorney, Agent, or Firm* — Holtz Holtz Goodman & Chick, PC

(57) ABSTRACT

A fermentation product (fermented food) that has high functionality by subjecting a fructan-containing material (in particular, a material including garlic or rakkyo containing fructan at a high concentration) directly to lactic acid fermentation without performing a heat treatment or an enzymatic treatment. More specifically, provided are: a fermentation product having an immunopotentiating effect, which is obtained by lactic acid fermentation of a fructan-containing material using a lactic acid bacterium *Lactobacillus plantarum* S506 strain (MITE BP-643) having fructan-utilizing ability, a mutant strain of the S506 strain having fructan-utilizing ability, or a strain isolated from *Lactobacillus plantarum* and having the same bacteriological properties as those of the S506 strain; and a fermented food which contains the fermentation product.

8 Claims, 4 Drawing Sheets

IMMUNOPOTENTIATING FERMENTED FOOD OBTAINED FROM FRUCTAN-CONTAINING FOOD

This application is a United States national phase application of International Application PCT/JP2010/052139 filed Feb. 15, 2010.

TECHNICAL FIELD

The present invention relates to a fermentation product, which is obtained by lactic acid fermentation of a fructan-containing material using a specific lactic acid bacterium strain having fructan-utilizing ability, and more particularly, to a fermentation product having an immunopotentiating effect.

Further, the present invention relates to a fermented food having an immunopotentiating effect, which contains the fermentation product.

BACKGROUND ART

A lactic acid bacterium has high ability to utilize a sugar source and utilizes glucose or a monosaccharide to perform lactic acid fermentation. In general, however, the lactic acid bacterium cannot ferment fructan which is an indigestible polysaccharide.

Fructan is an indigestible polysaccharide contained in a particularly large amount in garlic, rakkyo, and the like, and contents of the fructan in dried garlic and rakkyo are about 80% and about 70%, respectively.

Therefore, to increase the added value of garlic and rakkyo, an attempt has been made to directly ferment fructan contained at a high concentration (in particular, garlic), but has not succeeded.

In particular, garlic is expected to be used efficiently, and developments to use a variety of fermentations have been performed. Examples thereof include a case of carrying out fermentation by adding a small amount of garlic in a production process of wine (Patent Literature 1) and a case of carrying out fermentation by adding a large amount of a sugar to a small amount of garlic (Patent Literature 2).

Examples thereof further include a case of carrying cut fermentation using a 'koji mold' after deactivation of endogenous enzymes of garlic by heating (Patent Literature 3) and a case of carrying out lactic acid fermentation and propionic acid fermentation after heating and crushing garlic (Patent Literature 4).

However, none of the cases is a 'technology for direct fermentation without a heating treatment or an enzymatic treatment' of 'fructan' contained in garlic at a high concentration.

It should be noted that, with regard to physiological functions of garlic and rakkyo, many reports have been made on efficacy of an organic sulfur compound and saponin, but few reports have been made on fructan which accounts for a large percentage.

Therefore, it has been expected to develop a technology for giving high functionality or a technology for efficient use by fermenting fructan contained therein. In particular, an application to a 'lactic acid fermented food,' which is expected to have significantly high functionality, has been expected.

CITATION LIST

Patent Literature

[Patent Literature 1] JP 48-52995 A
[Patent Literature 2] JP 53-26361 A
[Patent Literature 3] JP 2002-154981 A
[Patent Literature 4] JP 2006-94853 A

SUMMARY OF INVENTION

Problem to be Solved by the Invention

In order to solve the above-mentioned problems, an object of the present invention is to provide a fermentation product (fermented food) that has 'high functionality' by subjecting a fructan-containing material (in particular, a material including garlic or rakkyo containing fructan at a high concentration) 'directly to lactic acid fermentation without performing a heat treatment or an enzymatic treatment.'

Means of Solving the Problem

The inventors of the present invention have found that it becomes possible to subject fructan in a fructan-containing material (in particular, a material including garlic or rakkyo containing fructan at a high concentration) 'directly to lactic acid fermentation without performing a heat treatment or an enzymatic treatment' by isolating and using a specific lactic acid bacterium strain having fructan-utilizing ability.

Further, the inventors of the present invention have found that the resultant fermentation product 'has an immunopotentiating effect' (has high functionality).

The inventors of the present invention have completed the present invention based on the findings.

That is, the present invention according to the first aspect relates to a fermentation product, which is obtained by lactic acid fermentation of a fructan-containing material using a lactic acid bacterium Lactobacillus plantarum S506 strain (NITE BP-643) having fructan-utilizing ability, a mutant strain of the S506 strain having fructan-utilizing ability, or a strain isolated from Lactobacillus plantarum and having the same bacteriological properties as those of the S506 strain.

The present invention according to the second aspect relates to a fermentation product according to the first aspect, in which the fructan-containing material includes one or more plants selected from garlic, rakkyo, chicory, sunchoke, dahlia, yacon, and burdock.

The present invention according to the third aspect relates to a fermentation product according to the first aspect, in which the fructan-containing material includes garlic.

The present invention according to the fourth aspect relates to a fermentation product according to any one of the first to third aspects, in which the fermentation product has an immunopotentiating effect.

The present invention according to the fifth aspect relates to a fermented food which contains the fermentation product according to any one of the first to fourth aspects.

Effects of the Invention

The lactic acid bacterium strain used in the present invention can perform efficient lactic acid fermentation using fructan as a sole sugar source without the presence of glucose or a monosaccharide, and hence the present invention enables providing a fermentation product 'having an immunopotentiating effect (having high functionality)' by subjecting a fructan-containing material (in particular, a material including garlic or rakkyo containing fructan at a high concentration) directly to lactic acid fermentation without performing a heat treatment or an enzymatic treatment.

The present invention enables providing a fermented food having an immunopotentiating effect, which contains the fermentation product.

Further, the present invention enables providing an immunopotentiator, which contains the fermentation product.

DESCRIPTION OF EMBODIMENTS

Figure 1:
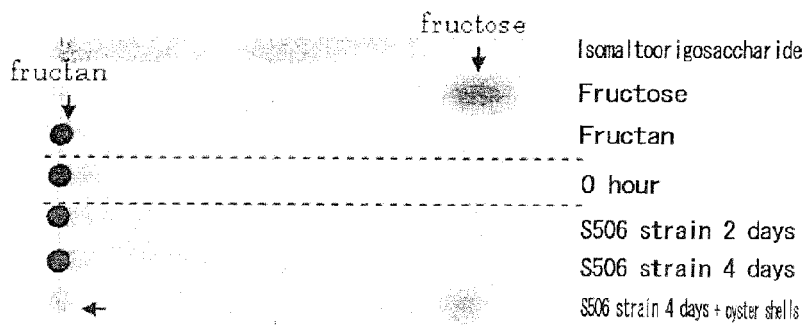
FIG. 1 An image showing fructan-utilizing ability of the S506 strain obtained in Preparation Example 1.

The present invention relates to a fermentation product, which is obtained by lactic acid fermentation of a fructan-containing material (in particular, a material including garlic containing fructan at a high concentration) using a specific lactic acid bacterium strain having fructan-utilizing ability, and more particularly, to a fermentation product having an immunopotentiating effect.

Further, the present invention relates to a fermented food having an immunopotentiating effect, which contains the fermentation product.

Fructan is a collective term of polysaccharides including fructose as a main constituent sugar, is a water-soluble dietary fiber, and is indigestible.

In the preset invention, the fructan-containing material is not limited as long as the material contains fructan, but the material is preferably one which contains fructan at a high concentration. Specifically, the material is preferably one including one or more plants selected from garlic, rakkyo, chicory, sunchoke, yacon, and burdock.

In particular, the material is preferably one including one or more plants selected from garlic and rakkyo, more preferably one including garlic.

It should be noted that plants belonging to the genus *Allium* such as garlic and rakkyo contain 'non-inulin type' fructan, which is excellent in solubility in water (in particular, solubility in cold water), and are preferably used as the material of the present invention.

Examples of the plants include a garlic bulb which is an edible part, a rakkyo bulb which is an edible part, a chicory root which is an edible part, a sunchoke tuber which is an edible part, a dahlia root, a yacon tuber, and a burdock root which is an edible part.

Examples of the fructan-containing material include: a product obtained by pulverizing, shredding, or grinding the above-mentioned plants; and a supernatant obtained by extracting water-soluble components after pulverizing, shredding, or grinding the above-mentioned plants.

For example, in the case of using garlic, there may be used: a product obtained by pulverizing, shredding, or grinding raw garlic; a squeeze of raw garlic; a product obtained by pulverizing, shredding, or grinding heated garlic; and a squeeze of heated garlic.

The fermentation product of the present invention is obtained by lactic acid fermentation of the fructan-containing material using a "lactic acid bacterium *Lactobacillus plantarum* S506 strain (NITE BP-643) having fructan-utilizing ability," a "mutant strain of the S506 strain having fructan-utilizing ability," or a "strain isolated from *Lactobacillus plantarum* and having the same bacteriological properties as those of the S506 strain."

It should be noted that, in the present invention, in the case of using a usual lactic acid bacterium (including usual *Lactobacillus plantarum*) other than the above-mentioned bacterial strains, it is impossible to obtain the fermentation product having an immunopotentiating effect by lactic acid fermentation of a fructan-containing material, in particular, a material including garlic containing fructan at a high concentration because fructan cannot be utilized completely or sufficiently.

The *Lactobacillus plantarum* S506 strain used in the present invention is a strain deposited with the Incorporated Administrative Agency, National Institute of Technology and Evaluation, Patent Microorganisms Depositary, having an address of 2-5-8, Kazusakamatari, Kisarazu-chi, Chiba-ken 292-0818, Japan, under "Accession No. NITE BP-643" on Sep. 2, 2008 and has almost the same bacteriological properties as those of *Lactobacillus plantarum* except that the strain "has fructan-utilizing ability."

In addition, in the present invention, a mutant strain of the S506 strain having fructan-utilizing ability may be used.

Further, in the present invention, a strain isolated from *Lactobacillus plantarum* and having the same bacteriological properties as those of the S506 strain may be used. The bacteriological properties of the isolated strain to be used are as follows: the strain has the same 'morphological characteristic' and 'ability to utilize a variety of sugars' mentioned in Preparation Example 1 below, preferably has the same 'base sequence of 16S rDNA' shown in Sequence Listing 1 in addition to the above-mentioned properties.

The lactic acid fermentation is performed until fructan contained in the above-mentioned material is sufficiently degraded into fructose.

Specifically, the fermentation is performed under anaerobic conditions at a temperature of 10 to 40° C., preferably 20 to 30° C.

The fermentation is desired to be performed at a pH of 3.0 to 7.0, preferably 4.0 to 5.5, particularly preferably about 5.0. It should be noted that pH adjustment may be performed by, for example, adding sterilized oyster shell powder to give a buffering effect for avoiding becoming acidic with progression of fermentation, resulting in maintaining the above-mentioned pH range.

The fermentation may be performed until fructan contained in the above-mentioned material is sufficiently degraded into fructose, and for example, the fermentation may be performed for 7 to 21 days.

When lactic acid fermentation is performed as mentioned above, the fermentation product of the present invention can be obtained.

The fermentation product of the present invention can be obtained as a product containing a sufficient amount of lactic acid bacteria.

Specifically, in the case where the fermentation product of the present invention is in a liquid form, a product containing $10^8$ to $10^{12}$/ml of lactic acid bacteria can be obtained.

Depending on the state or form of the material used, the resultant fermentation product can be obtained as: a liquid; a pulverized, shredded, or ground product; a paste; or a product in an original form of the material.

It should be noted that the products may be subjected to treatments such as pulverization and drying to prepare dried powders.

In the present invention, the immunopotentiating effect refers to an effect of improving functions for both natural immunity and acquired immunity.

The fermentation product of the present invention has the "immunopotentiating effect" and has the effect of improving functions for both natural immunity and acquired immunity, and is particularly effective for the immunopotentiating effect for the natural immunity.

It should be noted that the 'natural immunity' is a system for body's defense functions by cells of an inflammatory cell group including macrophages. For example, the natural immunity is an immune system for firstly protecting a body, such as discovery and removal of invasion of cold viruses, invasion of bacteria from wound sites due to cuts, and foreign matters such as cancer cells. In addition, the 'acquired immunity' is an immune system which can be developed by infection with a variety of antigens and is an immune system mainly based on antibodies.

Specifically, the fermentation product has, as 'natural immunity', an "effect of promoting nitric oxide (NO) production in macrophage cells (effect of activating macrophage cells)," an "effect of promoting IL-12 production in macrophage cells," and "activation of phagocytic ability of macrophage cells," all of which relate to improvement of activity of macrophage cells. It should be noted that the effect of promoting nitric oxide (NO) production in macrophage cells serves as one of indicators of enhancement of the natural immunity.

Further, the fermentation product further has, as 'natural immunity', an "effect of promoting proliferation of neutrophils," which relates to improvement of activity of granulocytes having a function to remove pathogenic bacteria by phagocytosis and sterilizing (the neutrophils accounts for 90% or more). It should be noted that cyclophosphamide, which is an anticancer drug, is known to have a side effect of immunity depression effect (decrease in neutrophils in blood), and even in administration of cyclophosphamide, the fermentation product of the present invention can suppress the decrease in neutrophils in blood.

Specifically, the fermentation product has, as 'acquired immunity', an "effect of promoting IgA secretion in saliva," which relates to intestinal immune barrier, and further has an "effect of promoting IFN-γ and IgA production from Peyer's patch cells."

It should be noted that the "effect of promoting IFN-γ production from Peyer's patch cells" includes an effect of promoting not only the acquired immunity but also the natural immunity.

In the present invention, the above-mentioned fermentation product may be used as a fermented food without further treatments but may be provided as a fermented food containing another material. For example, the fermented food may contain a material such as Asian ginseng, ginger, olive, clove, or guarana.

In addition, in the present invention, specifically, fermented foods such as health foods in the form of tablet or capsule, beverages, and confectionery can be obtained.

It should be noted that the above-mentioned fermentation product is desirably contained at a concentration of 0.1% or more in terms of dry weight.

It should be noted that, in the present invention, an "immunopotentiator" containing the above-mentioned fermentation product as an active ingredient can be obtained.

Examples of the form of the immunopotentiator include a powder, a liquid, a syrup, a capsule being filled with the immunopotentiator, a tablet obtained by blending with an excipient, a pill, and a granule.

To obtain the immunopotentiating effect, the "fermented food" and "immunopotentiator" may be taken once or twice a day at 0.1 to 2.0 g/dose in terms of dry weight of the fermentation product contained.

EXAMPLES

Hereinafter, the present invention is described by way of examples, but the technical scope of the present invention is not limited by the examples.

Preparation Example 1

Isolation and Selection of *Lactobacillus plantarum* S506 Strain (NITE BP-643)

(1) Isolation of Lactic Acid Bacterium Capable of Fermenting Garlic Fructan

First, screening of a lactic acid bacterium capable of degrading fructan was performed in a variety of foods derived from plants using fructan derived from garlic as a sugar source.

As a result, it was found that garlic fructan was fermented in 'pickled rakkyo' congeneric with garlic, and hence a lactic acid bacterium was isolated therefrom.

The bacterium was isolated using a universal and nutrient-rich LB plate, BCP-supplemented plate agar medium for lactic acid bacteria, or TYG plate, and the lactic acid bacterium was isolated from the pickled rakkyo.

From the pickled rakkyo, lactobacilli and lactococci as well as yeasts estimated as *Pichia* and *Hansenula* were detected. To perform further selection, a medium containing garlic squeeze as a sole nutrient source was used as a highly selective medium, and for example, a garlic fructan medium was originally prepared by mixing a small amount of yeast extract, garlic squeeze subjected to a proteolytic degradation treatment, trypton, and the like, and TYG plate was originally prepared using fructose as a sugar source to select lactic acid bacteria suitable for garlic fructan fermentation.

As a result, one lactic acid bacterium grew well in the medium containing garlic squeeze as a sole nutrient source, which was comparable to the growth in another nutrient-rich medium. The bacterium was found to be an obligatory anaerobic bacterium responsible for producing organic acid, be asporogenic, form clear-cut colonies with diameters of 1 to 2 mm, have no motility, and be a *bacillus* or a *streptococus/diplococcus* (short *bacillus*). Cloning was further performed to obtain an isolated strain with stable traits (S506 strain).

(2) Confirmation of Fructan-Utilizing Ability

The fructan-utilizing ability of the S506 strain was confirmed by the following method. FIG. 1 shows the results.

150 ml of water were added to 20 g of fructan-rich garlic extract powder, and culture was performed at 30° C. 100 μl of a solution of S506 bacterial cells cultured in a raw garlic squeeze medium were added as the fermentation starter (Sample p1-1), and the cells were cultured for two days (Sample p1-2).

After that, the cells were cultured for further two days (for four days in total) (Sample p1-3), or the cells were cultured for further two days (for four days in total) after addition of about 1 g of oyster shell powder (Sample p1-4).

The samples were separated by TLC to confirm degrees of fructan degradation. TLC was performed using a developing solvent having a composition of ethyl acetate, acetic acid, methanol, and water. After development, the thin layer was dried, and the respective spots were confirmed by coloring with an anis aldehyde reagent. FIG. 1 shows the results. It should be noted that FIG. 1 shows development from left to right.

As a result, after the culture for two days, slight fructan degradation was confirmed (Sample p1-2). It should be noted that in the sample cultured for four days without addition of the oyster shell powder after a lapse of two days, the degree of fructan degradation was just similar to that in the sample obtained after a lapse of two days (Sample p1-3).

In addition, in the sample in which the oyster shell powder was added after a lapse of two days, the number of viable cells in the S506 strain fermentation product increased to more than $10^9$/ml after a lapse of three days, and fructan was 'mostly degraded' after a lapse of four days (Sample p1-4).

The results suggest that the S506 strain utilizes fructan. In particular, it was found that fructan was utilized so long as an acidic condition did not become stronger.

(3) Identification of S506 Strain

Morphological Property

This bacterial strain was inoculated into MRS agar medium and cultured anaerobically at 30° C. for 48 hours, and morphological observation was performed for the bacterial cells after growth. As a result, the cells were found to have *bacillus* morphology (0.7 to 0.8×1.5 to 2.0 μm) and to be positive in Gram stain. The color of colonies was found to be milky white.

Moreover, this strain was found to be an obligatory anaerobic bacterium responsible for producing organic acid, be asporogenic, form clear-cut colonies with diameters of 1 to 2 mm, and have no motility.

Base Sequence

The base sequence of 16S rDNA (about 1,500 bp) was determined (see Sequence Listing 1), and the sequence was used to perform a homology search for a base sequence database. Moreover, 16S rDNA derived from a type strain of a related bacterial group, estimated from the results of the homology search, was obtained to perform a molecular phylogenetic analysis including 16S rDNA of the samples, and the samples were classified.

As a result, the base sequence of 16S rDNA was found to have high homology of 99% or more with *L. pentosus*, *L. plantarum*, and *L. paraplantarum*. In a homology search for an international base sequence database, the base sequence of 16S rDNA of the S506 strain was found to have high homology with *L. pentosus* and *L. plantarum*. This suggests that the S506 strain is closely related to *L. pentosus*, *L. plantarum*, and the like.

Accordingly, 16S rDNAs derived from *Lactbacillus* type strains mainly including the above-mentioned species were obtained to create a molecular phylogenetic tree. As a result of the molecular phylogenetic analysis, the S506 strain formed the same phylogenetic branch as *L. plantarum* and *L. pentosus*.

Test on Abilities of Utilizing Various Sugars

A test on abilities of utilizing various sugars was performed using a kit for assaying and identifying bacteria API 50 CHL (manufactured by bioMeriux). Culture was performed using MRS agar as a medium at a culture temperature of 30° C. in a culture period of 24 hours under anaerobic conditions. Table 1 shows the results.

TABLE 1

| Item | Substrate component | Utilization ability |
|---|---|---|
| 0 | (Control) | − |
| 1 | Glycerol | − |
| 2 | Erythritol | − |
| 3 | D-Arabinose | − |
| 4 | L-Arabinose | + |
| 5 | Ribose | + |
| 6 | D-Xylose | − |
| 7 | L-Xylose | − |
| 8 | Adonitol | − |
| 9 | β-Methyl-D-xyloside | − |
| 10 | Galactose | + |
| 11 | Glucose | + |
| 12 | Fructose | + |
| 13 | Mannose | + |
| 14 | Sorbose | + |
| 15 | Rhamnose | − |
| 16 | Dulcitol | − |
| 17 | Inositol | − |
| 18 | Mannitol | + |
| 19 | Sorbitol | + |
| 20 | α-Methyl-D-mannoside | − |
| 21 | α-Methyl-D-glucoside | − |
| 22 | N-Acetylglucosamine | + |
| 23 | Amygdalin | + |
| 24 | Arbutin | + |
| 25 | Esculin | + |
| 26 | Salicin | + |
| 27 | Cellobiose | + |
| 28 | Maltose | + |
| 29 | Lactose | + |
| 30 | Melibiose | + |
| 31 | Saccharose | + |
| 32 | Trehalose | + |
| 33 | Inulin | + |
| 34 | Melezitose | + |
| 35 | Raffinose | + |
| 36 | Starch | − |
| 37 | Glycogen | − |
| 38 | Xylitol | − |
| 39 | Gentiobiose | + |
| 40 | D-Turanose | + |
| 41 | D-Lyxose | − |
| 42 | D-Tagatose | − |
| 43 | D-Fucose | − |
| 44 | L-Fucose | − |
| 45 | D-Arabitol | − |
| 46 | L-Arabitol | − |
| 47 | Gluconate | + |
| 48 | 2-Ketogluconate | − |
| 49 | 5-Ketogluconate | − |

As a result, the S506 strain was found to ferment arabinose, ribose, galactose, fructose, and the like and not to ferment glycerol, xylose, and the like.

Moreover, the S506 strain exhibited growth ability at 15° C. Those properties 'correspond to those of *L. plantarum*' out of *L. pentosus* and *L. plantarum*.

In addition, from the viewpoint of no ability to utilize glycerol, D-xylose, and dulcitol, the S506 strain was different from *L. pentosus*.

Therefore, from the results of the phylogenetic analysis using the base sequences of 16S rDNAs and the results of the test on abilities of utilizing the sugars described above, the S506 strain was identified as "a novel lactic acid bacterium strain belonging to *Lactobacillus plantarum*."

This bacterium is a lactic acid bacterium characteristic in that the bacterium utilizes fructan and is very useful as a bacterium responsible for fermenting a fructan-containing material.

The lactic acid bacterium of the present invention, *Lactobacillus plantarum* S506 strain was deposited with the Incorporated Administrative Agency National Institute of Technology and Evaluation Patent Microorganism Depositary (2-5-8, Kazusa Kamatari, Kisarazu-shi, Chiba-ken, Japan) under accession No. NITE BP-643 on Sep. 2, 2008.

Preparation Example 2

Preparation of Bacterial Cells

*Lactobacillus plantarum* S506 strain (NITE BP-643) was cultured in a garlic fructan medium at 30° C. for three days.

The composition of the garlic fructan medium is as shown in Table 2. It should be noted that the garlic fructan was prepared by subjecting garlic to a heat treatment, extracting an extract from the heat-treated garlic, and purifying the extract by EtOH precipitation.

The resultant bacterial cells were inoculated into a small amount of TYF medium (which is a modified TIC medium prepared by using fructose instead of glucose) and cultured at 30° C. overnight. The culture was further inoculated into a TYF medium and cultured at 30° C. for eight hours. Bacterial cells (precipitates) were collected from the resultant culture and washed with physiological saline, to thereby prepare 'fermentation starter' for garlic.

TABLE 2

|  | Composition of garlic fructan medium (per L) |
|---|---|
| Garlic fructan (EtOH precipitates after heat treatment) | 50 g |
| Bromocresol purple | 0.06 g |
| $CaCO_3$ | 5 g |
| Agar | 10 g |

Example 1

Fermentation of Garlic

Water was added to 1 kg of garlic, and the mixture was heated at 80° C. for one hour. The supernatant was discarded, and about 700 ml of water were further added to the garlic, followed by homogenization.

Insoluble matter was removed from the resultant solution by centrifugation and the like, and the resultant solution was referred to as 'boiled garlic supernatant.'

The bacterial cells of the *L. plantarum* S506 strain obtained in Preparation Example 2 were added to the 'boiled garlic supernatant' as a fermentation starter and cultured at 30° C. for fermentation.

During culture, a small amount of the culture was sampled to measure a time-dependent change in pH, and the pH was adjusted to about pH 5.0 by adding sterilized oyster shell powder. 14 days later, culture was completed, to thereby obtain a fermented solution (fermentation product).

Progression of culture was confirmed by detecting degradation of fructan by utilization into fructose through TLC, and fermentation was completed when the amount of fructose produced and the number of the lactic acid bacterium cells reached sufficient values.

The thus-obtained fermented solution (fermentation product) was subjected to a heat treatment at 100° C. for 15 minutes and freeze-dried, to thereby obtain 'fermented garlic powder.'

Example 2

Fermentation of Raw Garlic

Raw garlic was homogenized, and the homogenate was filtered. The filtrate was sterilized by passing through a sterilized filter, to thereby prepare a substrate of fermentation.

The bacterial cells of the *L. plantarum* S506 strain obtained in Preparation Example 2 were added to the 'raw garlic squeeze solution' as a fermentation starter and cultured at 30° C. for fermentation.

During culture, a small amount of the culture was sampled to measure a time-dependent change in pH, and the pH was adjusted to about pH 5.0 by adding sterilized oyster shell powder. 14 days later, culture was completed, to thereby obtain a fermented solution (fermentation product).

Figure 2:
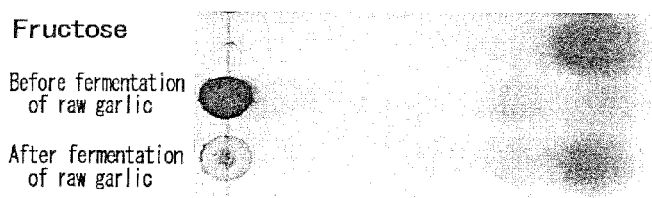
FIG. 2 An image showing the results of confirmation of fermentation of raw garlic by TLC in Example 2.

Progression of culture was confirmed by detecting degradation of fructan by utilization into fructose through TLC. TLC was performed in the same way as in Preparation Example 1. FIG. 2 shows the results of TLC for confirming progression of fermentation. It should be noted that FIG. 2 is an image showing development from left to right.

As a result, most of fructan present before fermentation of the raw garlic (the spot in the vicinity of the origin) was consumed after fermentation of the raw garlic, and production of fructose was confirmed.

Example 3

Effect of Promoting Nitric Oxide (NO) Production in Macrophage Cell by Fermented Garlic A mouse macrophage cell strain RAW 264.7 was used to measure macrophage-activating abilities based on nitric oxide (NO) production as an index. The RAW 264.7 cells were subcultured in a 10% FCS-supplemented RPMI-1640 medium before use. Culture was performed by subculturing the cells every three or four days at 0.5 to $1\times10^5$ cells/ml. The cells were cultured in a 5% $CO_2$ incubator at 37° C.

First, the number of the precultured RAW 264.7 cells was adjusted to $8\times10^5$ cells/ml, and the resultant cell suspension was added in an amount of 100 µl to each well of a 96-well flat bottom plate. The plate was transferred to a 5% $CO_2$ incubator at 37° C., and the cells were cultured for three hours until the cells adhered to and extended in bottoms of the wells. As a test sample, the fermented garlic powder obtained in Example 1 was used as 'fermented garlic,' and a solution obtained by adding the fermented garlic to the cell culture at a final concentration of 100 µg/ml was used as a maximum content. Moreover, solutions containing the fermented garlic at lower contents of 50 µg/ml, 10 µg/ml, 5 µg/ml, and 2 µg/ml were tested.

As a comparative control sample, an unfermented boiled garlic supernatant was used as unfermented garlic and was used by adjusting the final concentration in the cell culture to 100 µg/ml, 50 µg/ml and 10 µg/ml. In addition, as a positive control, a lipopolysaccharide (LPS purified from *Pantoea agglomerans*) was used at a final concentration of 100 ng/ml.

The prepared test solutions were added to corresponding wells each in an amount of 100 µl and stirred using a plate shaker for 10 seconds, and the plate was transferred to a 5% $CO_2$ incubator at 37° C., followed by culture for 20 hours.

After completion of culture, 50 μl of a culture supernatant were transferred from each well to another 96-well flat bottom plate. A Griess reagent prepared was added to each well in an amount of 50 μl, and the plate was incubated at room temperature for 10 minutes, followed by measurement of an absorbance at a wavelength of 550 nm using a plate reader.

Figure 3:
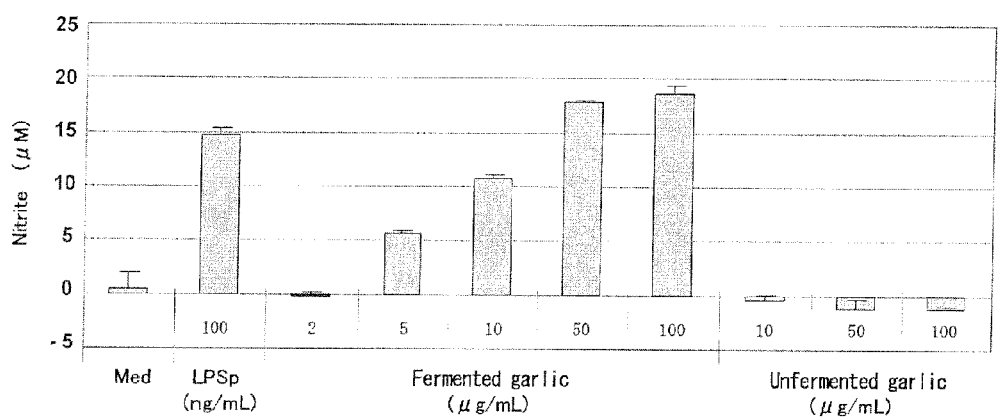
FIG. 3 A graph showing the results of a test on nitric oxide (NO) production ability of macrophages in Example 3.

FIG. 3 shows results of the test for examining abilities to produce nitric oxide (NO) from macrophage at the respective concentrations of the fermented garlic, unfermented garlic, and LPS.

As a result, as shown in FIG. 3, in the case of the fermented garlic, nitric oxide (NO) production was enhanced concentration-dependently, while in the case of the unfermented garlic, nitric oxide (NO) production was not observed at any concentration. That is, it was found that the fermentation imparted an nitric oxide (NO)-producing ability.

Example 4

Effect of Promoting IL-12 Production in Macrophage Cell by Fermented Garlic

A mouse macrophage cell strain J774.1 was used to measure macrophage-activating abilities based on IL-12 production as an index. The J774.1 cells were subcultured in a 10% FBS-supplemented DMEM medium before use. Culture was performed by subculturing the cells every three days at 0.5 to $1 \times 10^7$ cells/ml. The cells were cultured in a 5% $CO_2$ incubator at 37° C.

The number of the precultured J774.1 cells was adjusted to $1 \times 10^5$ cells/ml, and the resultant cell suspension was added in an amount of 800 μl to each well of a 48-well flat bottom plate. As samples, the 'fermented garlic' (the fermented garlic powder obtained in Example 1), 'unfermented garlic' (the unfermented boiled garlic supernatant), and 'fructan' were separately added at a final concentration of 10 μg/ml, and BPS was further added to each well at a final concentration of 1 μg/ml. The plate was transferred to a 5% $CO_2$ incubator at 37° C., and the cells were cultured for 24 hours. After completion of culture, a culture supernatant was sampled from each well, and IL-12 was measured by ELISA.

Figure 4:
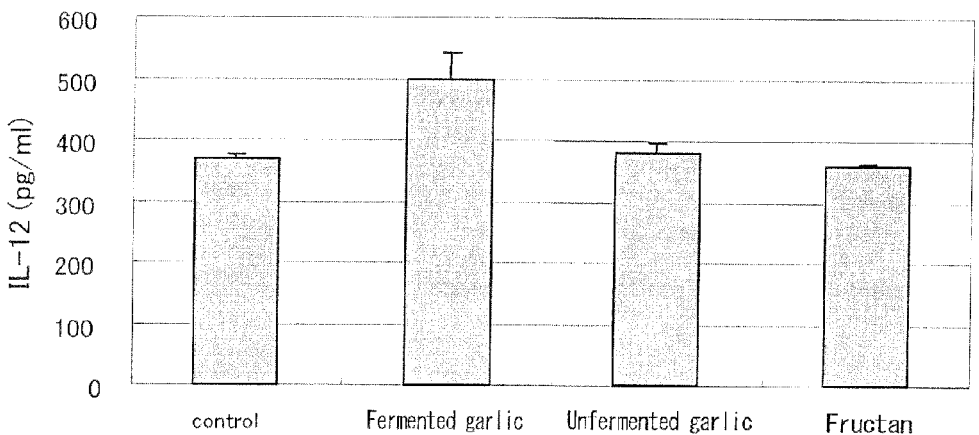
FIG. 4 A graph showing the results of a test on IL-12 production ability of macrophages in Example 4.

FIG. 4 shows the results of the test for examining abilities of the fermented garlic, unfermented garlic, and fructan to produce IL-12 from macrophage.

As a result, in the cases of the unfermented garlic and fructan, production of IL-12 was not observed, while in the case of the fermented garlic, the IL-12-producing ability was enhanced.

Example 5

Activation of Mouse Macrophage Cell Phagocytic Ability by Fermented Garlic

Macrophage cells used in this example were prepared from seven- or eight-week-old male ICR mice (purchased from Japan SLC, Inc.) which had been subjected to a 1-week period of preliminary rearing.

That is, the mice were killed by removing the heads, and 5 ml of cooled PBS were injected into their abdomens. Then, the abdomens were massaged for about three minutes to suspend cells, and the injected PBS was collected and centrifuged. The resultant cells were washed with PBS and suspended in 10% FBS-supplemented DMEM medium at $1 \times 10^6$ cells/ml, and the suspensions were inoculated into 35-mm dishes each in an amount of 1 ml. The dishes were transferred to a 5% $CO_2$ incubator at 37° C., and the cells were cultured for 1.5 hours. Subsequently, samples, i.e., 'LPS,' the 'fermented garlic' (the fermented garlic powder obtained in Example 1), and 'unfermented garlic' (the unfermented boiled garlic supernatant) were added thereto. LPS was adjusted so as to have a final concentration of 2 μg/ml, and the fermented garlic and unfermented garlic were each adjusted so as to have a final concentration of 200 μg/ml.

After addition of the samples, the cells were incubated in 5% $CO_2$ at 37° C. for 30 minutes. After that, the media were removed, and the cells were washed twice with PBS. A 10% PBS-supplemented DMEM medium was newly added in an amount of 1 ml, and zymosan derived from yeast was added at a final concentration of 200 μg/ml, followed by incubation in 5% $CO_2$ at 37° C. for two hours. After completion of culture, the cells were washed to remove unreacted zymosan and media, and May-Giemsa stain was performed to prepare smears, followed by microscopic visualization to determine phagocytic rates. The phagocytic rates were each calculated as a ratio of the number of cells that phagocytosed one or more zymosan to the total number of cells.

Figure 5:
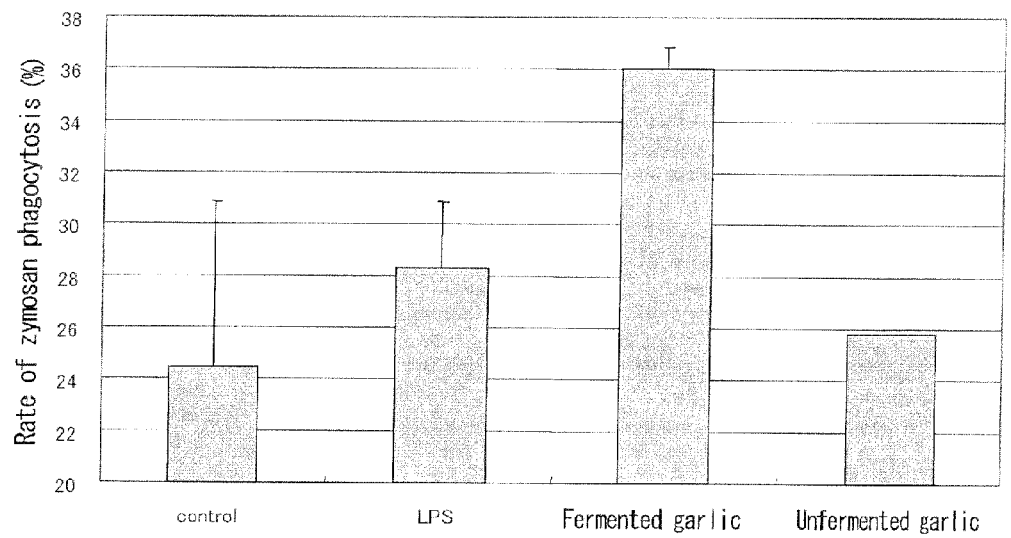
FIG. 5 A graph showing the results of a test on ability of macrophage to engulf foreign matter in Example 5.

FIG. 5 shows the results of the test on activation of macrophage phagocytic ability by LPS, fermented garlic and unfermented garlic.

As a result, in the case of the unfermented garlic, the phagocytic ability did not change, while in the case of the fermented garlic, the effect of activating phagocytic ability was higher than that of LPS, and the value was significantly ($p<0.01$) higher than that of the control group.

Example 6

Effect of Promoting IFN-γ and IgA Production from Mouse Peyer's Patch Cells by Fermented Garlic Seven- or eight-week-old female BALB/c mice (purchased from Japan SLC, Inc.) were used as experimental animals after a 1-week period of preliminary rearing. The mice were killed, and the small intestines were removed to collect Peyer's patches in a RPMI-1640 medium. The collected Peyer's patches were dispersed by pressing, and the resultant cell suspensions were passed through nylon meshes, followed by washing with a RPMI-1640 medium. The cells were resuspended in a 5% or 10% FBS-supplemented RPMI 1640 medium, to thereby obtain Peyer's patch cells.

The resultant Peyer's patch cells were adjusted to $1 \times 10^6$ cells/ml with the above-mentioned medium and inoculated into a 96-well flat bottom plate. The plate was transferred to a 5% $CO_2$ incubator at 37° C. and cultured for three hours, and the same samples as in Example 5 were added thereto. The cells were cultured in a 5% $CO_2$ incubator at 37° C., and ELISA was performed to measure INF-γ using the culture supernatant collected on the third day of culture and IgA using the culture supernatant collected on the seventh day of culture.

Figure 6:
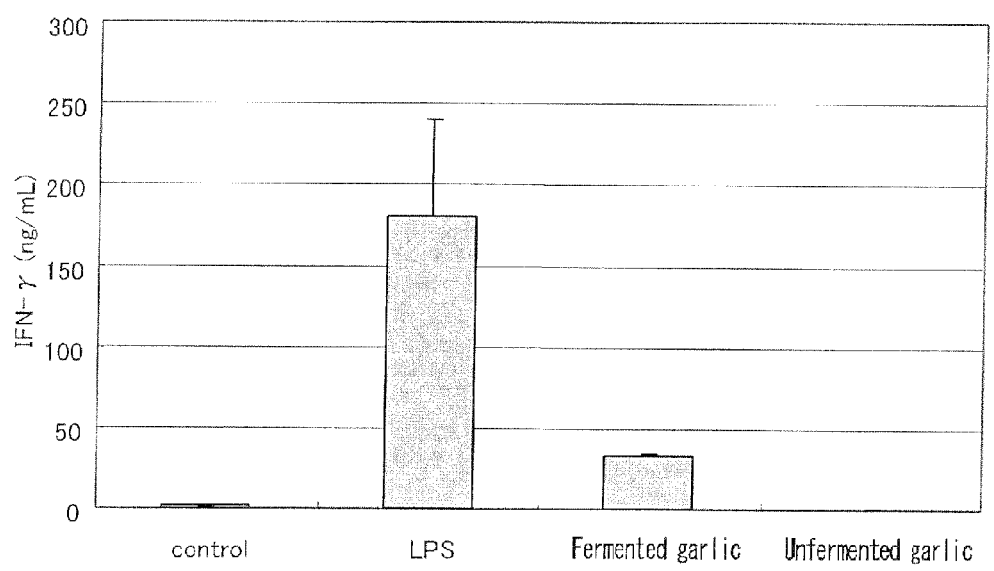
FIG. 6 A graph showing the results of a test on promotion of IFN-γ production from mouse Peyer's patch cells in Example 6.
Figure 7:
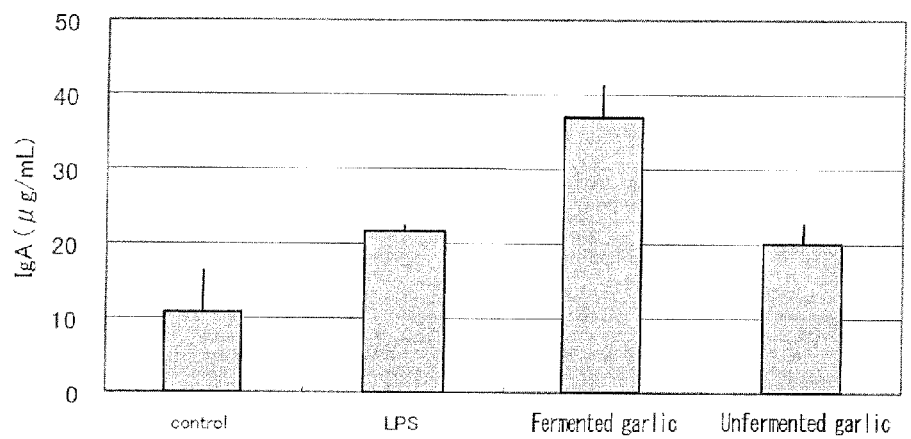
FIG. 7 A graph showing the results of a test on promotion of IgA production from mouse Peyer's patch cells in Example 6.

FIGS. 6 and 7 show the results of the test on promotion of IFN-γ and IgA production from the Peyer's patch cells by LPS, fermented garlic, and unfermented garlic.

As a result, in the cases of the control group and unfermented garlic, INF-γ was produced in small amounts, while in the cases of the LPS and the fermented garlic, INF-γ was produced in significantly ($p<0.01$) large amounts compared with the control group. In the cases of the LPS and the unfermented garlic, IgA was produced in significantly ($p<0.05$) large amounts compared with the control group, while in the case of the fermented garlic, IgA was produced in a still larger amount (p<0.01 compared with the control group, LPS, and unfermented garlic).

Example 7

Effect of Promoting Mouse Neutrophil Proliferation by Fermented Garlic

Seven-week-old female BALB/c mice (purchased from Japan SLC, Inc.) were used as experimental animals after a 1-week period of preliminary rearing.

The 'fermented garlic' (the fermented garlic powder described in Example 1) was prepared and orally administered to the mice at 2 g/kg once a day over nine days using stomach tubes (group C). As a control group and a comparative control group, 'physiological saline' was orally administered instead of the fermented garlic (groups A and B).

On the third day from starting of oral administration 'cyclophosphamide' was prepared and intraperitoneally administered in an amount of 100 mg/kg to each of the comparative group (group B) and the fermented garlic-administered group (group C) to compromise immunity. On the eighth to tenth day from starting of the fermented garlic administration, blood was collected from the tail veins, and May-Giemsa stain was performed to prepare smears, followed by microscopic visualization of blood cell morphology to determine the numbers of neutrophils.

Figure 8:
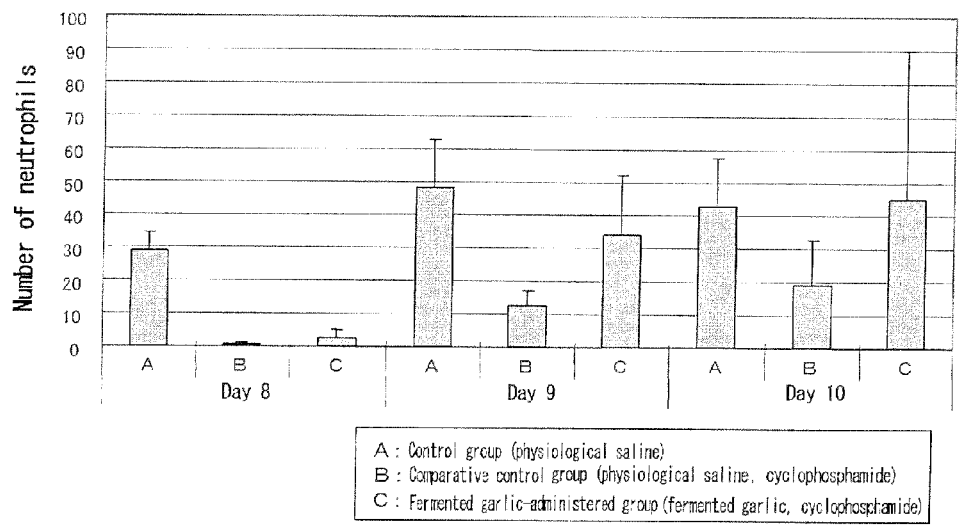
FIG. 8 A graph showing the results of a test on mouse neutrophil proliferation-promoting effect in Example 7.

FIG. 8 shows the results of the test on the effect of promoting neutrophil proliferation by the fermented garlic for mice with immunity compromised by cyclophosphamide.

As a result, in the cases of the comparative control group (group B) and fermented garlic-administered group (group C), on the eighth day from starting of administration, neutrophils were found to decrease significantly (p<0.01) compared with the control group (group A). On the ninth day and tenth day, the numbers of the neutrophils of the fermented garlic-administered group (group C) were not significantly different from those of the control group (group A), while the number of the neutrophils of the comparative control group (group B) remained significantly (p<0.01) low.

This reveals that the fermented garlic promotes proliferation of the neutrophils.

Example 8

Effect of Promoting IgA Secretion in Human Saliva by Fermented Garlic

Several volunteers were allowed to freely ingest 0.75 g of the 'fermented garlic' (the fermented garlic powder obtained in Example 1) once a day for five weeks, and ingestion was stopped for the following two weeks.

Saliva was collected with cotton before ingestion, five weeks after starting of ingestion, and two weeks after stopping of ingestion (seven weeks after starting of experiment) and centrifuged to prepare saliva IgA measurement samples, and measurement was performed by ELISA.

Figure 9:
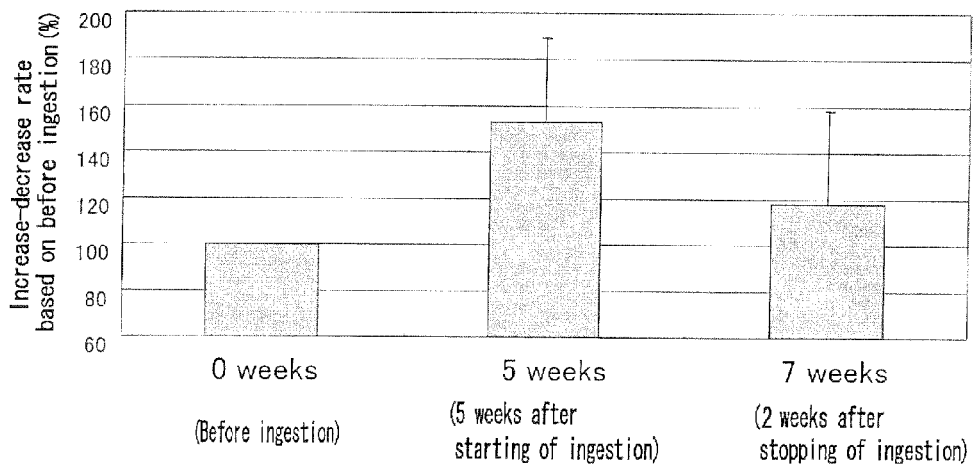
FIG. 9 A graph showing the results of a test on IgA secretion-promoting effect in human saliva in Example 8.

FIG. 9 shows the results of the test on the effect of promoting secretion of IgA in human saliva by the fermented garlic.

As a result, secretion of IgA was found to increase significantly (P<0.05) by the five-week ingestion compared with before ingestion. Moreover, secretion of IgA was found to decrease two weeks after stopping of ingestion.

Example 9

Activation of Ability of Human Neutrophil by Fermented Garlic to Engulf Foreign Matter In the same way as in Example 8, volunteers were allowed to ingest the 'fermented garlic' (the fermented garlic powder obtained in Example 1). After ingestion for five weeks, ingestion was stopped for the following two weeks, and then ingestion was restarted for two weeks.

Peripheral blood was collected five weeks after starting of ingestion, two weeks after stopping of ingestion (seven weeks after starting of experiment), one week after restart of ingestion (eight weeks after starting of experiment), and two weeks after restart of ingestion (nine weeks after starting of experiment), and mixed with 2 mg/ml zymosan in an equal amount, and the mixtures were allowed to react at 26° C. for 30 minutes to phagocytize zymosan. After reaction, May-Giemsa stain was performed to prepare smears, and zymosan phagocytic rates were determined by microscopic visualization.

Figure 10:
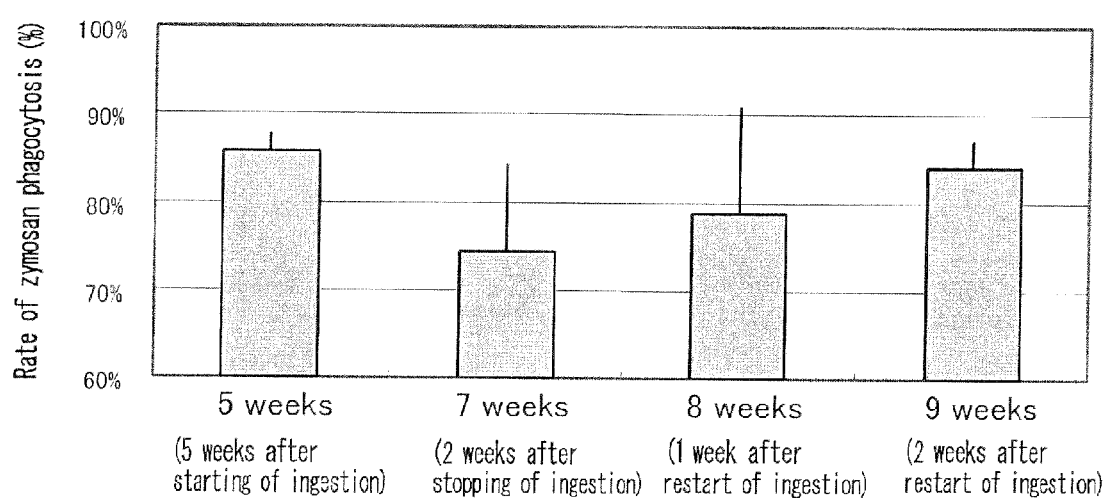
FIG. 10 A graph showing the results of a test on activation of ability of human neutrophils to engulf foreign matter in Example 9.

FIG. 10 shows the results of the test to examine whether the ability of human neutrophil to engulf foreign matter was activated by the fermented garlic.

As a result, the phagocytic rate which was high five weeks after staring of ingestion was found to decrease significantly (2<0.05) two weeks after stopping ingestion (seven weeks after starting of experiment), but increase again by restart of ingestion.

Example 10

Fermentation of Rakkyo

Rakkyo was immersed in water containing a small amount of NaCl to perform extraction for about two weeks. The resultant solution was dialyzed to remove salts. The thus-obtained dialysate was sterilized by boiling, and bacterial cells of L. plantarum S506 strain obtained in Preparation Example 2 were added thereto as a fermentation starter and cultured at 30° C. for fermentation.

During culture, a small amount of culture was sampled to measure a time-dependent change in pH, and the pH was adjusted to about pH 5.0 by adding sterilized oyster shell powder. One week later, culture was completed when pH reached about 4.0, to thereby obtain a fermented solution (fermentation product).

At this time, the number of the lactic acid bacterial cells was found to be about $10^9$/ml.

Example 11

Fermentation of Fructan from Chicory or Sunchoke

Fructan was prepared from chicory or sunchoke by pulverization and water-extraction, and the bacterial cells of L. plantarum S506 strain obtained in Preparation Example 2 were added thereto as a fermentation starter and cultured at 30° C. for fermentation.

During culture, a small amount of culture was sampled to measure a time-dependent change in pH, and the pH was adjusted to about pH 5.0 by adding sterilized oyster shell powder. 14 days later, culture was completed, to thereby obtain a fermented solution (fermentation product) of fructan from chicory and a fermented solution (fermentation product) of fructan from sunchoke.

Fermentation of fructan was confirmed by detecting degradation of fructan by utilization into fructose through TLC.

INDUSTRIAL APPLICABILITY

The lactic acid bacterium strain found in the present invention allows the provision of a technology useful for giving high functionality to a fructan-containing food.

The fermented food containing a lactic acid fermentation product from a fructan-containing material in the present invention can be used as a health food having an immunopotentiating effect and can be used in the food industry.

In addition, the immunopotentiator containing a lactic acid fermentation product from a fructan-containing material in the present invention can be used in the medicinal field.

Reference to Deposited Biological Material

NITE BP-643

The invention claimed is:

1. A fermentation product, which is obtained by lactic acid fermentation of a raw material which consists of garlic using a lactic acid bacterium *Lactobacillus plantarum* S506 strain (NITE BP-643) having a fructan-utilizing ability.

2. The fermentation product according to claim 1, wherein the fermentation product has an immunopotentiating effect.

3. A fermented food which contains the fermentation product according to claim 1.

4. A fermented food which contains the fermentation product according to claim 2.

5. The fermented product according to claim 1, wherein the strain is *Lactobacillus plantarum* S506 strain (NITE BP-643).

6. The fermented product according to claim 1, wherein the fermentation is carried out at a temperature of 20 to 40° C. for 7 to 21 days.

7. The fermented product according to claim 1, wherein the garlic comprises a supernatant obtained by extracting water-soluble components after pulverizing, shredding or grinding the garlic.

8. The fermented product according to claim 7, wherein the strain is *Lactobacillus plantarum* S506 strain (NITE BP-643), and the fermentation is carried out at a temperature of 20 to 40° C. for 7 to 21 days.

\* \* \* \* \*

SEQUENCE LISTING

```
<160> NUMBER OF SEQ ID NOS: 1

<210> SEQ ID NO 1
<211> LENGTH: 1531
<212> TYPE: DNA
<213> ORGANISM: Lactobacillus plantarum S506

<400> SEQUENCE: 1
tggagagttt gatcctggct caggacgaac gctggcggcg tgcctaatac atgcaagtcg      60
aacgaactct ggtattgatt ggtgcttgca tcatgattta catttgagtg agtggcgaac     120
tggtgagtaa cacgtgggaa acctgcccag aagcggggga taacacctgg aaacagatgc     180
taataccgca taacaacttg daccgcatgg tccgagtttg aaagatggct tcggctatca     240
cttttggatg gtcccgcggc gtattagcta gatggtgrgg taacggctca ccatggcaat     300
gatacgtagc cgacctgaga gggtaatcgg ccacattggg actgagacac ggcccaaact     360
cctacgggag gcagcagtag ggaatcttcc acaatggacg aaagtctgat ggagcaacgc     420
cgcgtgagtg aagaagggtt tcggctcgta aaactctgtt gttaaagaag aacatatctg     480
agagtaactg ttcaggtatt gacggtattt aaccagaaag ccacggctaa ctacgtgcca     540
gcagccgcgg taatacgtag gtggcaagcg ttgtccggat ttattgggcg taaagcgagc     600
gcaggcggtt ttttaagtct gatgtgaaag ccttcggctc aaccgaagaa gtgcatcgga     660
aactgggaaa cttgagtgca gaagaggaca gtggaactcc atgtgtagcg gtgaaatgcg     720
tagatatatg gaagaacacc agtggcgaag gcggctgtct ggtctgtaac tgacgctgag     780
gctcgaaagt atgggtagca aacaggatta gataccctgg tagtccatac cgtaaacgat     840
gaatgctaag tgttggaggg tttccgccct tcagtgctgc agctaacgca ttaagcattc     900
cgcctgggga gtacggccgc aaggctgaaa ctcaaaggaa ttgacggggg cccgcacaag     960
cggtggagca tgtggtttaa ttcgaagcta cgcgaagaac cttaccaggt cttgacatac    1020
tatgcaaatc taagagatta gacgttccct tcggggacat ggatacaggt ggtgcatggt    1080
tgtcgtcagc tcgtgtcgtg agatgttggg ttaagtcccg caacgagcgc aacccttatt    1140
atcagttgcc agcattaagt tgggcactct ggtgagactg ccggtgacaa accggaggaa    1200
ggtggggatg acgtcaaatc atcatgcccc ttatgacctg ggctacacac gtgctacaat    1260
ggatggtaca acgagttgcg aactcgcgag agtaagctaa tctcttaaag ccattctcag    1320
ttcggattgt aggctgcaac tcgcctacat gaagtcggaa tcgctagtaa tcgcggatca    1380
gcatgccgcg gtgaatacgt tcccgggcct tgtacacacc gcccgtcaca ccatgagagt    1440
ttgtaacacc caaagtcggt ggggtaacct tttaggaacc agccgcctaa ggtgggacag    1500
atgattaggg tgaagtcgta acaaggtagc c                                  1531
```